(12) United States Patent
Nagata et al.

(10) Patent No.: US 11,610,576 B2
(45) Date of Patent: Mar. 21, 2023

(54) RESIN MATERIAL FOR ACOUSTIC LENS, ACOUSTIC LENS, ACOUSTIC WAVE PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

(71) Applicant: FUJIFILM Corporation, Tokyo (JP)

(72) Inventors: Yuzo Nagata, Kanagawa (JP); Yoshihiro Nakai, Kanagawa (JP); Toshihide Yoshitani, Kanagawa (JP); Shigeki Uehira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 743 days.

(21) Appl. No.: 16/554,019

(22) Filed: Aug. 28, 2019

(65) Prior Publication Data

US 2019/0380680 A1 Dec. 19, 2019

Related U.S. Application Data

(63) Continuation of application No. PCT/JP2018/007869, filed on Mar. 1, 2018.

(30) Foreign Application Priority Data

Mar. 9, 2017 (JP) .............. JP2017-044807

(51) Int. Cl.
*C08G 77/16* (2006.01)
*G10K 11/30* (2006.01)
*A61B 8/00* (2006.01)
*C08L 63/00* (2006.01)
*C08L 83/04* (2006.01)
*A61B 8/12* (2006.01)
*C08G 77/26* (2006.01)
*C08G 77/14* (2006.01)
*C08G 77/12* (2006.01)
*C08G 77/20* (2006.01)

(52) U.S. Cl.
CPC .............. *G10K 11/30* (2013.01); *A61B 8/445* (2013.01); *C08L 63/00* (2013.01); *C08L 83/04* (2013.01); *A61B 8/12* (2013.01); *A61B 8/4272* (2013.01); *C08G 77/12* (2013.01); *C08G 77/14* (2013.01); *C08G 77/16* (2013.01); *C08G 77/20* (2013.01); *C08G 77/26* (2013.01); *C08L 2203/20* (2013.01)

(58) Field of Classification Search
CPC .......... C08L 83/04; C08L 63/00; C08L 67/02; C08G 77/04; C08G 18/06; C08G 77/16; C08G 77/26; C08G 8/10; A61B 5/0095; A61B 8/12
See application file for complete search history.

(56) References Cited

U.S. PATENT DOCUMENTS

| | | | |
|---|---|---|---|
| 7,074,844 B2 * | 7/2006 | Iwata ............... | C08G 18/62 524/14 |
| 2007/0049686 A1 * | 3/2007 | Bauchet .............. | C09D 175/04 525/123 |
| 2009/0062411 A1 * | 3/2009 | Rappmann .............. | C08L 53/02 524/505 |
| 2009/0068473 A1 * | 3/2009 | Van Wessel ......... | C09D 163/00 428/416 |
| 2010/0193961 A1 * | 8/2010 | Konishi ................ | C08L 83/00 257/773 |
| 2017/0009072 A1 * | 1/2017 | Kobayashi ......... | C08G 59/4085 |

FOREIGN PATENT DOCUMENTS

| | | | |
|---|---|---|---|
| JP | 2015-202212 A | | 11/2015 |
| JP | 2016-213666 A | | 12/2016 |
| JP | 2016213666 | * | 12/2016 |
| JP | 2017-12435 A | | 1/2017 |
| WO | 2015159603 | * | 10/2015 |

OTHER PUBLICATIONS

JP 2016 213666 machine translaltion (2016).*
International Search Report dated May 29, 2018 from the International Searching Authority in counterpart International Application No. PCT/JP2018/007869.
Written Opinion dated May 29, 2018 from the International Bureau in counterpart International Application No. PCT/JP2018/007869.
International Preliminary Report on Patentability dated Aug. 7, 2019 from the International Bureau in counterpart International Application No. PCT/JP2018/007869.

* cited by examiner

*Primary Examiner* — Kuo Liang Peng
(74) *Attorney, Agent, or Firm* — Sughrue Mion, PLLC

(57) ABSTRACT

Provided are a resin material for an acoustic lens including a resin (a) containing at least one of an epoxy group, a carbon-carbon double bond group, a methylol group, or a phenolic hydroxyl group; and a resin (b) containing a structural unit having a polysiloxane bond, and an acoustic lens, an acoustic wave probe, an acoustic wave measurement apparatus, an ultrasound diagnostic apparatus, a photoacoustic wave measurement apparatus, and an ultrasound endoscope in which the resin material is used.

19 Claims, 1 Drawing Sheet

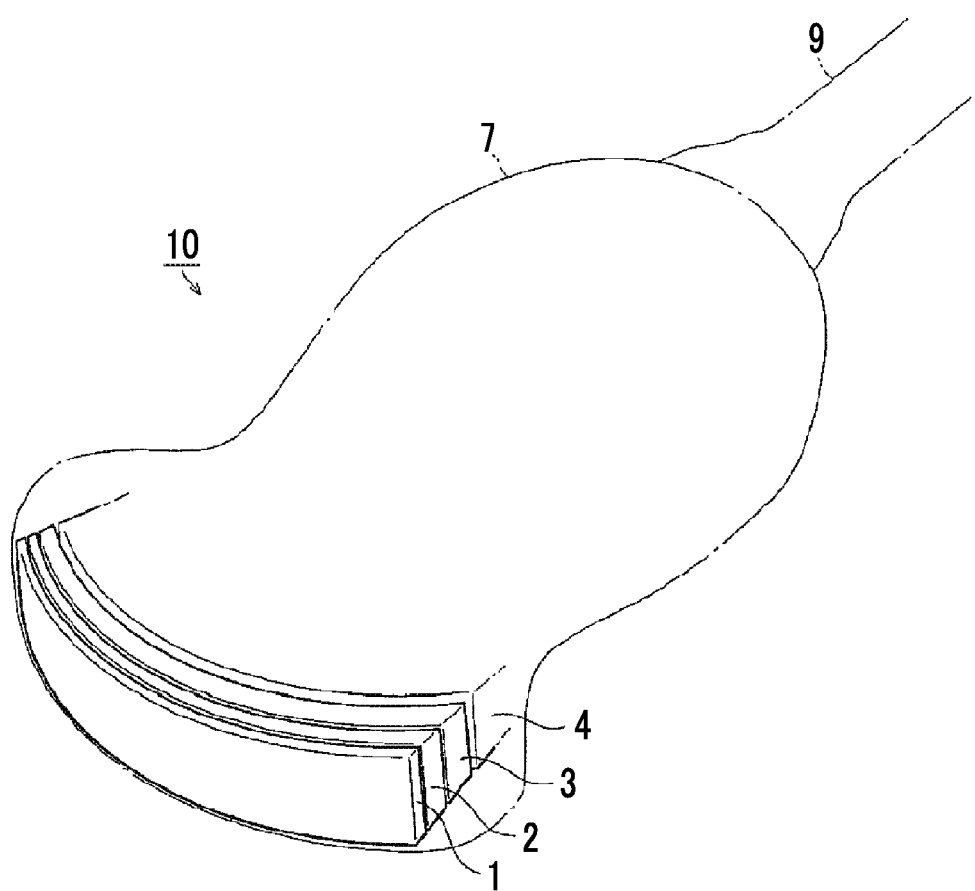

RESIN MATERIAL FOR ACOUSTIC LENS, ACOUSTIC LENS, ACOUSTIC WAVE PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

CROSS-REFERENCE TO RELATED APPLICATIONS

This application is a Continuation of PCT International Application No. PCT/JP2018/007869 filed on Mar. 1, 2018, which claims priority under 35 U.S.C. § 119 (a) to Japanese Patent Application No. 2017-044807 filed in Japan on Mar. 9, 2017. Each of the above applications is hereby expressly incorporated by reference, in its entirety, into the present application.

BACKGROUND OF THE INVENTION

1. Field of the Invention

The present invention relates to a resin material for an acoustic lens, an acoustic lens, an acoustic wave probe, an acoustic wave measurement apparatus, an ultrasound diagnostic apparatus, a photoacoustic wave measurement apparatus, and an ultrasound endoscope.

2. Description of the Related Art

In the acoustic wave measurement apparatus, an acoustic wave probe is used which irradiates a test object or a site (hereinafter, also simply referred to as an object) with an acoustic wave, receives a reflected wave (echo) thereof, and outputs a signal. An electrical signal converted from the reflected wave which has been received by this acoustic wave probe is displayed as an image. Accordingly, the interior of the test object is visualized and observed.

Acoustic waves, such as ultrasonic waves and photoacoustic waves, which have an appropriate frequency in accordance with a test object and/or measurement conditions, are selected as the acoustic waves.

For example, the ultrasound diagnostic apparatus transmits an ultrasonic wave to the interior of a test object, receives the ultrasonic wave reflected by the tissues inside the test object, and displays the received ultrasonic wave as an image. The photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave and generates heat in a case where the test object is irradiated with an electromagnetic wave pulse of visible light, near infrared light, microwave, or the like.

The acoustic wave measurement apparatus performs transmission and reception of an acoustic wave on a living body (typically, the human body) which is a test object. Therefore, it is necessary to fulfill requirements such as consistency in the acoustic impedance within the living body and decrease in acoustic attenuation.

A probe for an ultrasound diagnostic apparatus (also referred to as an ultrasound probe) which is a kind of acoustic wave probe includes an acoustic lens which is a portion coming into contact with a living body, an acoustic matching layer, a piezoelectric element (transducer) which transmits and receives an ultrasonic wave, and a backing material. For example, JP2015-202212A discloses a resin composition which is used as a backing material for an ultrasonic transducer, containing an epoxy resin, a vulcanizing agent, and an ion exchanger, and capable of providing a backing material for an ultrasonic transducer having excellent sterilization resistance and high acoustic characteristics.

SUMMARY OF THE INVENTION

An ultrasonic wave generated from the piezoelectric element in the above-described ultrasound probe is incident on the living body after being transmitted through the acoustic lens. In a case where the difference between acoustic impedance (density x acoustic velocity) of the acoustic lens and acoustic impedance of the living body is large, the ultrasonic wave is reflected by the surface of the living body. Therefore, the ultrasonic wave is not efficiently incident on the living body. In addition, it is desirable that ultrasonic attenuation of the acoustic lens is low in order to transmit and receive the ultrasonic wave with high sensitivity. Furthermore, since the acoustic lens is required to have durability in use during diagnosis using an ultrasonic probe, it is desirable that the acoustic lens has an excellent tear strength.

In view of the above-described circumstances, an object of the present invention is to provide a resin material for an acoustic lens with which it is possible to obtain an acoustic lens, of which the acoustic impedance is close to an acoustic impedance value of a living body (in the case of a living body, 1.4 to $1.7\times10^6$ kg/m$^2$/sec) and the acoustic attenuation decreases even at a high frequency (for example, 10 MHz) and which has an excellent tear strength.

In addition, another object of the present invention is to provide an acoustic lens using the above-described resin material for an acoustic lens as a constituent material, an acoustic wave probe, an acoustic wave measurement apparatus, an ultrasound diagnostic apparatus, a photoacoustic wave measurement apparatus, and an ultrasound endoscope.

The above-described objects are solved by the following means.

<1> A resin material for an acoustic lens comprising: a resin (a) containing at least one of an epoxy group, a carbon-carbon double bond group, a methylol group, or a phenolic hydroxyl group; and a resin (b) containing a structural unit having a polysiloxane bond.

<2> The resin material for an acoustic lens according to <1>, in which the resin (a) is at least one of an epoxy resin, a phenolic resin, a urea resin, a melamine resin, or an unsaturated polyester.

<3> The resin material for an acoustic lens according to <1> or <2>, in which at least a part of the resin (a) is bonded to at least a part of the resin (b).

<4> The resin material for an acoustic lens according to <3>, in which a bonding portion between the resin (a) and the resin (b) has an epoxy ring-opened structure formed by a reaction between an epoxy group contained in the resin (a) and an amino group and/or a carboxy group contained in the resin (b).

<5> The resin material for an acoustic lens according to <3>, in which the bonding portion between the resin (a) and the resin (b) has a carbon-carbon bond formed by polymerization between the carbon-carbon double bond group contained in the resin (a) and a carbon-carbon double bond group contained in the resin (b).

<6> The resin material for an acoustic lens according to <3>, in which the bonding portion between the resin (a) and the resin (b) has an ether bond and/or an imino bond formed by a reaction between the methylol group contained in the resin (a) and a hydroxy group and/or the amino group contained in the resin (b).

<7> The resin material for an acoustic lens according to <3>, in which the bonding portion between the resin (a) and the resin (b) has an epoxy ring-opened structure formed by a reaction between a phenolic hydroxyl group contained in the resin (a) and an epoxy group contained in the resin (b).

<8> The resin material for an acoustic lens according to <1> or <2>, further comprising: a blended resin of the resin (a) and the resin (b).

<9> The resin material for an acoustic lens according to any one of <1> to <8>, in which a ratio of a content mass mb of the resin (b) to a ratio of a content mass ma of the resin (a) is ma:mb=30:70 to 70:30.

<10> The resin material for an acoustic lens according to any one of <1> to <9>, which is used for an acoustic wave probe lens of which an acoustic impedance is less than or equal to $1.7 \times 10^6$ kg/m$^2$/sec.

11> An acoustic lens comprising: the resin material for an acoustic lens according to any one of <1> to <10>.

<12> The acoustic lens according to <11>, in which a density is greater than or equal to 1.05 g/cm$^3$.

<13> A acoustic wave probe comprising: the acoustic lens according to <11> or <12>.

<14> An acoustic wave measurement apparatus comprising: the acoustic wave probe according to <13>.

<15> An ultrasound diagnostic apparatus comprising: the acoustic wave probe according to <13>.

<16> A photoacoustic wave measurement apparatus comprising: the acoustic lens according to <11> or <12>.

<17> An ultrasound endoscope comprising: the acoustic lens according to <11> or <12>.

In the present specification, when there are plurality of substituents, linking groups, repeating structures, and the like (hereinafter, referred to as substituents) represented by specific reference numerals, or when a plurality of substituents and the like are simultaneously defined, unless otherwise specified, the substituents may be the same as or different from each other. The same applies to definition of the number of substituents and the like. In addition, when a plurality of substituents and the like are near (particularly, adjacent to) each other, unless otherwise specified, they may be linked to each other to form a ring. In addition, the ring, for example, an aliphatic ring, an aromatic ring, or a hetero ring may be further condensed to form a condensed ring.

In the present specification, in a case of defining the number of carbons of a certain group, the number of carbon atoms means a number of carbons of whole groups. That is, in a case where this group is in a form further having a substituent, it means a total number of carbon atoms including this substituent.

In addition, a group (for example, an alkyl group) specified by each group may further have a substituent. In addition, an "Si—H group" means a group having three bonds on a silicon atom in addition to —H, but the description of the bonds is not repeated and the notation is simplified.

In addition, in the present specification, "to" means a range including numerical values denoted before and after "to" as a lower limit value and an upper limit value.

Unless otherwise specified, the mass average molecular weight in the present specification refers to a value (in terms of polystyrene) measured through gel permeation chromatography (GPC).

The mass average molecular weight can be measured specifically using TETRAHYDROFURAN (manufactured by Wako Pure Chemical Industries, Ltd.) as an eluent, TSKgel (registered trademark), G3000HXL+TSKgel (registered trademark), and G2000HXL as columns, and a RI detector under the conditions of a temperature of 23° C. and a flow rate of 1 mL/min after preparing a GPC apparatus HLC-8220 (which is a trade name manufactured by TOSOH CORPORATION).

The acoustic lens produced using the resin material for an acoustic lens of the embodiment of the present invention has an acoustic impedance close to an acoustic impedance value of a living body, has a decreasing acoustic attenuation even at a high frequency, and has an excellent tear strength. The acoustic lens, the acoustic wave probe, the acoustic wave measurement apparatus, the ultrasound diagnostic apparatus, the photoacoustic wave measurement apparatus, and the ultrasound endoscope of the embodiment of the present invention contains a resin material for an acoustic lens which has the above-described excellent performances.

BRIEF DESCRIPTION OF THE DRAWINGS

FIG. 1 is a perspective transparent view of an example of a convex ultrasound probe which is an aspect of an acoustic wave probe.

DESCRIPTION OF THE PREFERRED EMBODIMENTS

<<Resin Material for Acoustic Lens>>

The resin material for an acoustic lens of the embodiment of the present invention contains a resin (a) containing at least one of an epoxy group, a carbon-carbon double bond group, a methylol group, or a phenolic hydroxyl group and a resin (b) containing a structural unit having a polysiloxane bond. Hereinafter, the "resin material for an acoustic lens of the embodiment of the present invention" is also simply referred to as a "resin material". In addition, the "resin (a) containing at least one of an epoxy group, a carbon-carbon double bond group, a methylol group, or a phenolic hydroxyl group" is also simply referred to as a "resin (a)". In addition, the "resin (b) containing a structural unit having a polysiloxane bond" is also simply referred to as a "resin (b)".

The resin material for an acoustic lens of the embodiment of the present invention may be consisting of the resins or may contain commonly used components or any components, such as filler, a catalyst, a solvent, a dispersant, a pigment, a dye, an antistatic agent, a flame retardant, and a thermal conductivity enhancer, which express an additional action in addition to the resins. In a case where the resin material for an acoustic lens of the embodiment of the present invention is formed of two or more components, in general, it is preferable that the resin composition for an acoustic wave probe is in a form of a composition in which the components are homogeneously mixed with each other.

The shape of the resin material for an acoustic lens itself of the embodiment of the present invention is not particularly limited. The resin material for an acoustic lens may be mixed with a solvent or the like to have fluidity, or may have a pellet shape.

By molding the resin material for an acoustic lens of the embodiment of the present invention, it is possible to obtain an acoustic lens having all excellent characteristics of an acoustic impedance close to an acoustic impedance value of a living body, decrease in acoustic attenuation (particularly acoustic attenuation at a high frequency), and an excellent tear strength. Although the reason is unclear, it is considered that resins (a) and (b) form a bond through heat or the like in a case of molding to form a cross-linked structure and the resin (a) and the resin (b) are more uniformly mixed with each other, thereby suppressing phase separation between the resin (a) and the resin (b) and improving acoustic sensitivity of an acoustic lens. In addition, the resin (a) has a relatively high density in many cases, and therefore, it is considered that the resin (a) is advantageous to make acoustic impedance of the acoustic lens close an acoustic impedance value of a living body. In addition, the formation of the above-described cross-linked structure also contributes to improvement of the tear strength of the acoustic lens.

(1) Resin (a) Containing at Least One of Epoxy Group, Carbon-Carbon Double Bond Group, Methylol Group, or Phenolic Hydroxyl Group The resin (a) used in the resin material of the embodiment of the present invention is not particularly limited as long as it is a silicone resin containing at least one of an epoxy group, a carbon-carbon double bond group, a methylol group, or a phenolic hydroxyl group.

The mass average molecular weight of the resin (a) is not particularly limited, but is preferably 100 to 1,000,000, more preferably 500 to 100.000, and particularly preferably 1,000 to 10.000.

The functional group equivalent (that is, the mass average molecular weight of the resin (a) per functional group) of the resin (a) is not particularly limited, but is preferably 10 to 100,000 g/eq, more preferably 50 to 10,000 g/eq, and particularly preferably 100 to 1,000 g/eq.

It is possible to improve the mechanical strength of the acoustic lens by making the resin (a) used in the resin material of the embodiment of the present invention have a high strength. Therefore, the resin (a) is preferably a thermosetting resin and more preferably at least one of an epoxy resin, a phenolic resin, a urea resin, a melamine resin, or unsaturated polyester. Hereinafter, each resin will be described.

(Epoxy Resin)

Specific examples of epoxy resins include a bisphenol A-type epoxy resin, a bisphenol F-type epoxy resin, a phenol novolac-type epoxy resin, a cresol novolac-type epoxy resin, an alicyclic epoxy resin, a glycidyl ester-type epoxy resin, and a glycidyl amine-type epoxy resin.

Specific examples of bisphenol A-type epoxy resins include EPICLON HM-101 (trade name manufactured by DIC CORPORATION), EPICLON 840 (trade name manufactured by DIC CORPORATION), and JER 828 (trade name manufactured by Mitsubishi Chemical Corporation).

Specific examples of bisphenol F-type epoxy resins include EPICLON 830 (trade name manufactured by DIC CORPORATION), 4004P (trade name manufactured by Mitsubishi Chemical Corporation), and JER807 (trade name manufactured by Mitsubishi Chemical Corporation).

Specific examples of phenol novolac-type epoxy resins include YDPN-638 (trade name manufactured by NIPPON STEEL & SUMIKIN CHEMICAL CO., LTD.) and N-770 (trade name manufactured by DIC CORPORATION).

Specific examples of cresol novolac-type epoxy resins include EPICLON N-660 (trade name manufactured by DIC CORPORATION) and YDCN-700-3 (trade name manufactured by NIPPON STEEL & SUMIKIN CHEMICAL CO., LTD.).

Specific examples of alicyclic epoxy resins include CELLOXIDE 2012P (trade name manufactured by Daicel Corporation) and Syna-Epoxy28 (trade name manufactured by Synasia).

Specific examples of glycidyl ester-type epoxy resins include EPOX-AH R508 (trade name manufactured by Printec Co.) and EPOX-AH R540 (trade name manufactured by Printec Co.).

Specific examples of glycidyl amine-type epoxy resins include EP-3950S (trade name manufactured by ADEKA) and SKE-3 (trade name manufactured by TECHNOSET).

(Phenolic Resin)

Specific examples of phenolic resins include PHENOLITE TD-2131 (trade name manufactured by DIC CORPORATION) and CP506F (trade name manufactured by ASAHI YUKIZAI CORPORATION).

(Urea Resin)

Specific examples of urea resins include FLEAMIN M (trade name manufactured by Daiwa) and CU (trade name manufactured by Panasonic Corporation).

(Melamine Resin)

Specific examples of melamine resins include FLEAMIN Z (trade name manufactured by Daiwa) and ME-J (trade name manufactured by Panasonic Corporation).

(Unsaturated Polyester)

Examples of unsaturated polyester include a diallyl phthalate resin and a vinyl ester resin (epoxy acrylate resin). Specific examples of diallyl phthalate resins include CD-J-710 (trade name manufactured by Hitachi Chemical Co., Ltd.) and DP-1300 (trade name manufactured by ASAHI YUKIZAI CORPORATION). Specific examples of vinyl ester resins include UE-8410 (trade name manufactured by DIC CORPORATION) and 8026 (trade name manufactured by U-PICA Company, Ltd.). Another example thereof includes U-PICA 4015 (trade name manufactured by U-PICA Company, Ltd.).

Unsaturated polyester contains a monomer which has an ester bond and two or more carbon-carbon double bond groups in a molecule and in which a polymerization reaction using the carbon-carbon double bond groups proceeds in a case of preparing a resin material for an acoustic lens through a kneading step to be described below so as to become unsaturated polyester. Examples of this monomer include a polyfunctional (meth)acrylate monomer having an ester bond in a molecule (for example, ARONIX M-400 (trade name manufactured by TOAGOSEI CO., LTD.).

(2) Resin (b) Containing Structural Unit Having Polysiloxane Bond

A resin (b) is not particularly limited as long as it has a structural unit having a polysiloxane bond as a structural unit constituting a resin. In addition, the polysiloxane bond may be introduced into either a main chain and/or a side chain in a structural unit, but is preferably introduced into a main chain.

Silicone having a polysiloxane bond can result from a reaction between first silane (for example, a first silicon-containing group such as a first alkoxysilyl group or a first hydroxysilyl group) and second silane (for example, a second silicon-containing group such as a second alkoxysilyl group or a second hydroxysilyl group).

The resin (b) used for the resin material of the embodiment of the present invention is not particularly limited as long as it has a structural unit having a polysiloxane bond.

The mass average molecular weight of the resin (b) is not particularly limited, but is preferably 100 to 1,000,000, more preferably 500 to 100,000, and particularly preferably 1,000 to 50,000.

In addition, the resin (b) preferably has a functional group reacting with an epoxy group, a carbon-carbon double bond group, and/or a methylol group which are contained in the resin (a). Examples of such functional groups include an amino group, a carboxy group, a carbon-carbon double bond group, a hydroxy group, a Si—H group, and an epoxy group.

The functional group equivalent (that is, the mass average molecular weight of the resin (b) per functional group) of the resin (b) is not particularly limited, but is preferably 100 to 100,000 g/eq, more preferably 5,000 to 10,000 g/eq, and particularly preferably 1,000 to 5,000 g/eq.

Polysiloxane (hereinafter, also referred to as polysiloxane (A)) represented by General Formula (A) is preferable as the resin (b).

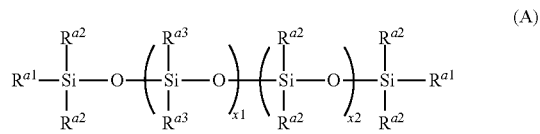

$R^{a1}$ to $R^{a3}$ in General Formula (A) represents an alkyl group, a cycloalkyl group, an alkenyl group, a phenyl group, an amino group, a hydroxy group, a (meth)acryloyloxy group, a carboxy group, or an epoxy group, x1 and x2 each independently represent an integer of 1 or more.

The number of carbon atoms in an alkyl group in $R^{a1}$ to $R^{a3}$ is preferably 1 to 10, more preferably 1 to 4, still more preferably 1 or 2, and particularly preferably 1. Examples of the alkyl group include a methyl group, an ethyl group, a propyl group, an isopropyl group, a butyl group, an isobutyl group, a hexyl group, an octyl group, a 2-ethylhexyl group, and a decyl group.

The number of carbon atoms in a cycloalkyl group in $R^{a1}$ and $R^{a3}$ is preferably 3 to 10, more preferably 5 to 10, and still more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group in $R^{a1}$ to $R^{a3}$ is preferably 2 to 10, more preferably 2 to 4, and still more preferably 2. Examples of the alkenyl group include a vinyl group, an allyl group, and a butenyl group.

An amino group, a hydroxy group, a (meth)acryloyloxy group, or a carboxy group may be bonded to a silicon atom through a linking group or a bond. Examples of linking groups or bonds include an alkylene group (preferably having 1 to 5 carbon atoms), an arylene group (preferably having 5 to 12 carbon atoms), a heteroarylene group (preferably having 3 to 12 carbon atoms), an ether bond, an ester bond, or an amide bond.

The alkyl group, the cycloalkyl group, the alkenyl group, and the phenyl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a1}$ is preferably an alkyl group, an alkenyl group, an amino group, a hydroxy group, a (meth)acryloyloxy group, or a carboxy group is preferable and an alkenyl group, an amino group, a hydroxy group, a (meth)acryloyloxy group, or a carboxy group is more preferable. The alkyl group is preferably an alkyl group having 1 to 4 carbon atoms and more preferably methyl. The alkenyl group is preferably an alkenyl group having 2 to 4 carbon atoms and more preferably vinyl.

$R^{a2}$ and $R^{a3}$ are preferably an alkyl group, an alkenyl group, or an phenyl group, more preferably an alkyl group having 1 to 4 carbon atoms, a vinyl group, or a phenyl group, and still more preferably a methyl group.

x1 is preferably an integer of 1 to 3,000 and more preferably an integer of 5 to 1,000.

x2 is preferably an integer of 1 to 3,000, and more preferably an integer of 40 to 1,000.

In the present invention, each of the repeating units "—Si($R^{a3}$)$_2$—O—" and "—Si($R^{a2}$)$_2$—O—" in General Formula (A) may exist in a block-polymerized form or may be in a form in which the repeating units exist randomly.

Examples of polysiloxane represented by General Formula (A) include KF-96-50cs, KF-8012, KF-6003, KF-2012, and X-22-163A (all are trade names) manufactured by Shin-Etsu Chemical Co., Ltd. In addition, DMS series (for example, DMS-V41, DMS-A15, DMS-R18, DMS-C23, DMS-CA21), ECMS-227, DBL-C31, and EBP-234 (all are trade names) manufactured by GELEST, INC.

The polysiloxane (A) represented by General Formula (A) may be used singly or in a combination of two or more thereof.

Polyorganosiloxane having two or more Si—H groups in a molecular chain can be used as the resin (b). In a case where the resin (a) has a carbon-carbon double bond, it can form a bond with Si—H of the resin (b).

<Polysiloxane (B) Having Two or More Si—H Groups in Molecular Chain>

The polysiloxane (B) having two or more Si—H groups in a molecular chain that can be used in the present invention (hereinafter, also simply referred to as polysiloxane (B)) has two or more Si—H groups in a molecular chain. Here, in a case where the polysiloxane (B) has a "—SiH$_2$—" structure, the number of Si—H groups in the "—SiH$_2$—" structure is counted as two. In addition, in a case where the polysiloxane (B) has a "—SiH$_3$—" structure, the number of Si—H groups in the "—SiH$_3$—" structure is counted as three.

In a case where there are two or more Si—H groups in a molecular chain, it is possible to crosslink polysiloxane having at least two carbon-carbon double bonds.

There is a linear structure and a branched structure in the polysiloxane (B), and the linear structure is preferable.

In addition, the polysiloxane (B) preferably has a phenyl group, and the content of the phenyl group is not particularly limited. The content of the phenyl group is, for example, 20 to 80 mol % and preferably 30 to 70 mol % from the viewpoint of mechanical strength in a case where an acoustic lens is made.

Here, the content of the phenyl group is mol % of a phenyl group-containing siloxane unit in a case where all units constituting the polysiloxane (B) are set to 100 mol %. In a case where all Si atoms of Si in a Si—O unit and at a terminal which constitute a main chain are substituted with at least one phenyl group, the content becomes 100 mol %.

The "unit" of polysiloxane refers to Si atoms in a Si—O unit and at a terminal which constitute a main chain.

The Si—H equivalent of the polysiloxane (B) is preferably less than or equal to 1.300 g/mol and more preferably less than or equal to 500 g/mol in addition to the above-described functional group equivalent. In addition, the Si—H equivalent is preferably greater than or equal to 50 g/mol and more preferably greater than or equal to 100 g/mol.

In a case where the acoustic lens of the embodiment of the present invention has a bulky phenyl group, it is possible to increase the acoustic velocity, the hardness, and the specific gravity. For this reason, it is possible to increase the acoustic impedance.

The polysiloxane (B) which has a linear structure and two or more Si—H groups in a molecular chain is preferably polysiloxane represented by General Formula (B).

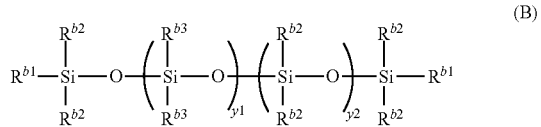

In General Formula (B), $R^{b1}$ and $R^{b2}$ each independently represent a hydrogen atom, an alkyl group, a cycloalkyl group, an aryl group, or —O—Si$(R^{b6})_2(R^{b5})$. $R^{b5}$ and $R^{b6}$ each independently represent a hydrogen atom, an alkyl group, a cycloalkyl group, or an aryl group. $R^{b3}$ and $R^{b4}$ each independently represent a hydrogen atom, an alkyl group, a cycloalkyl group, an alkenyl group, an aryl group, or —O—Si$(R^{b8})_2(R^{b7})$. $R^{b7}$ and $R^{b8}$ each independently represent a hydrogen atom, an alkyl group, a cycloalkyl group, an alkenyl group, or an aryl group, y1 represents an integer of 0 or more and y2 represents an integer of 1 or more. Here, each of the groups of $R^{b1}$ to $R^{b8}$ may further be substituted with a substituent. However, there are two or more Si—H groups in a molecular chain.

An alkyl group and a cycloalkyl group in $R^{b1}$ and $R^{b2}$ are synonymous with an alkyl group and a cycloalkyl group in $R^{a1}$ to $R^{a3}$, and preferred ranges thereof are also the same as each other. An alkyl group, a cycloalkyl group, and an alkenyl group in $R^{b3}$ and $R^{b4}$ are synonymous with an alkyl group, a cycloalkyl group, and an alkenyl group in $R^{a1}$ to $R^{a3}$, and preferred ranges thereof are also the same as each other. The number of carbon atoms of an aryl group in $R^{b1}$ to $R^{b4}$ is preferably 6 to 12, more preferably 6 to 10, and still more preferably 6 to 8. Examples of the aryl group include a phenyl group, a tolyl group, and a naphthyl group.

An alkyl group, a cycloalkyl group, and an aryl group in $R^{b5}$ and $R^{b6}$ of —O—Si$(R^{b6})_2(R^{b5})$ are synonymous with an alkyl group, a cycloalkyl group, and an aryl group in $R^{b1}$ and $R^{b2}$, and preferred ranges thereof are also the same as each other.

An alkyl group, a cycloalkyl group, an alkenyl group, and an aryl group in $R^{b7}$ and $R^{b8}$ of —O—Si$(R^{b8})_2(R^{b7})$ are synonymous with an alkyl group, a cycloalkyl group, an alkenyl group, and an aryl group in $R^{b3}$ and $R^{b7}$, and preferred ranges thereof are also the same as each other.

$R^{b1}$ and $R^{b2}$ are preferably a hydrogen atom, an alkyl group, an aryl group, or —O—Si$(R^{b6})_2(R^{b5})$, and more preferably a hydrogen atom, an alkyl group having 1 to 4 carbon atoms, a phenyl group, or —O—Si(CH$_3$)$_2$H.

$R^{b3}$ and $R^{b4}$ are preferably a hydrogen atom, an alkyl group, an alkenyl group, an aryl group, or —O—Si$(R^{b8})_2$ $(R^{b7})$, and more preferably a hydrogen atom, an alkyl group having 1 to 4 carbon atoms, a vinyl group, a phenyl group, or —O—Si(CH$_3$)$_2$H.

Among them, $R^{b1}$ and $R^{b2}$ are preferably a hydrogen atom, an alkyl group, or an aryl group, more preferably a hydrogen atom or an alkyl group, and still more preferably a hydrogen atom or a methyl group. In addition, a combination of $R^{b1}$ as a hydrogen atom and $R^{b2}$ as a methyl group is preferable.

$R^{b3}$ is preferably a hydrogen atom, an alkyl group, an alkenyl group, an aryl group, or —O—Si$(R^{b8})_2(R^{b7})$, more preferably a hydrogen atom or an alkyl group, and particularly preferably a hydrogen atom.

$R^b$ is preferably a hydrogen atom, an alkyl group, an alkenyl group, an aryl group, or —O—Si$(R^{b8})(R^{b7})$, more preferably a hydrogen atom, an alkyl group, or an aryl group, still more preferably a hydrogen atom, a methyl group, or a phenyl group, still more preferably a methyl group or a phenyl group, and particularly preferably a phenyl group.

y1 is preferably an integer of 1 or more.

y1+y2 is preferably an integer of 5 to 2,000, more preferably an integer of 7 to 1.000, still more preferably an integer of 10 to 50, and particularly preferably an integer of 15 to 30.

Each of "—Si$(R^{b3})(R^{b2})$—O—" and "—Si$(R^{b4})(R^{b2})$—O—" in General Formula (B) in the present invention may exist in a block-polymerized form in polysiloxane or may be in a form in which they exist randomly in polysiloxane.

As a combination of $R^{b1}$ to $R^{b3}$, a combination of a hydrogen atom or an alkyl group having 1 to 4 carbon atoms as $R^{b1}$, an alkyl group having 1 to 4 carbon atoms as $R^{b2}$, and a hydrogen atom as $R^{b3}$ is preferable and a combination of an alkyl group having 1 to 4 carbon atoms as $R^{b1}$, an alkyl group having 1 to 4 carbon atoms as $R^{b2}$, and a hydrogen atom as $R^{b3}$ is more preferable.

Examples of the polysiloxane (B) with a linear structure include HMS-151 (Si—H equivalent of 490 g/mol), HMS-301 (Si-Hl equivalent of 245 g/mol), HMS-501 (Si—H equivalent of 135 g/mol), and HMS-064 (Si—H equivalent of 1,240 g/mol) which are methylhydrosiloxane-dimethylsiloxane copolymers (trimethylsiloxy terminated), HMS-991 (Si—H equivalent of 67 g/mol) which is a methylhydrosiloxane polymer (trimethylsiloxy terminated), and HPM-502 (Si—H equivalent of 165 g/mol) which is a methylhydrosiloxane-phenylmethylsiloxane copolymer (hydride terminated) (all are trade names of GELEST, INC.).

It is preferable that both the linear structure and the branched structure have no vinyl group from the viewpoint of preventing the progress of a cross-linking reaction within a molecule. Among these, it is preferable that the branched structure has no vinyl group.

The polysiloxane (B) which has a branched structure and two or more Si—H groups in a molecular chain has a branched structure and two or more hydrosilyl groups (Si—H groups).

The specific gravity is preferably 0.9 to 0.95.

The polysiloxane (B) with a branched structure is preferably represented by Average Composition Formula (b).

Average Composition Formula (b): $[H_a(R^{b9})_{3-a}SiO_{1/2}]_{y3}$ $[SiO_{4/2}]_{y4}$ Here, $R^{b9}$ represents an alkyl group, a cycloalkyl group, an alkenyl group, or an aryl group, a represents 0.1 to 3, and y3 and y4 each independently represent an integer of 1 or more.

An alkyl group, a cycloalkyl group, an alkenyl group, and an aryl group in $R^{b9}$ are synonymous with an alkyl group, a cycloalkyl group, an alkenyl group, and an aryl group in $R^{b3}$ and $R^{b4}$, and preferred ranges thereof are also the same as each other.

a is preferably 1.

The content ratio of a hydrosilyl group represented by a/3 is preferably greater than 0.1 and less than 0.6 and more preferably greater than 0.1 and less than 0.4.

In contrast, in a case of representing the polysiloxane (B) with a branched structure using a chemical structural formula, polysiloxane in which —O—Si(CH$_3$)$_2$(H) is bonded to a Si atom constituting a main chain is preferable and polysiloxane having a structure represented by General Formula (Bb) is more preferable.

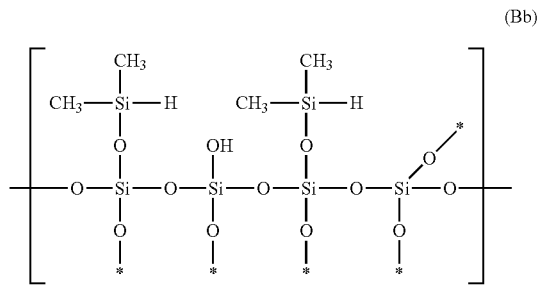

(Bb)

In General Formula (Bb), * means a bond with at least a Si atom of siloxane.

Examples of the polysiloxane (B) with a branched structure include HQM-107 (trade name of Hydride Q Resin manufactured by GELEST, INC.) and HDP-111 (trade name of polyphenyl-(dimethylhydroxy)siloxane (hydride terminated), [(HM$_{c2}$SiO)(C$_6$H$_5$Si)O]: 99 to 100 mol % manufactured by GELEST, INC.).

Me is CH$_3$.

The polysiloxane (B) having two or more Si—H groups in a molecular chain in the present invention may be used singly, or in combination of two or more thereof. In addition, the polysiloxane (B) with a linear structure and the polysiloxane (B) with a branched structure may be used in combination.

In order to further improve the acoustic sensitivity of an acoustic lens by further reducing phase separation between the resin (a) and the resin (b) of the resin material of the embodiment of the present invention, it is preferable that at least a part of the resin (a) is bonded to at least a part of the resin (b). Hereinafter, a resin in which at least a part of the resin (a) is bonded to at least a part of the resin (b) may be referred to as a "composite resin". Hereinafter, preferred embodiments of the composite resin will be described.

Examples of the above-described composite resin include the following composite resins:

A composite resin having an epoxy ring-opened structure formed by a reaction between an epoxy group contained in the resin (a) and an amino group and/or a carboxy group contained in the resin (b);

A composite resin having an epoxy ring-opened structure formed by a reaction between a phenolic hydroxyl group contained in the resin (a) and an epoxy group contained in the resin (b);

A composite resin having a carbon-carbon bond formed by polymerization between a carbon-carbon double bond group contained in the resin (a) and a carbon-carbon double bond group contained in the resin (b): and A composite resin having an ether bond and/or an imino bond [—N(R)—, in which R represents a hydroxy group or a substituent] formed by a reaction between a methylol group contained in the resin (a) and a hydroxy group and/or an amino group contained in the resin (b).

These composite resins are preferable from the viewpoint of improving sensitivity of an acoustic lens by reducing phase separation because the resin (a) react with the resin (b) with high efficiency. Among these, the composite resin having a carbon-carbon bond formed by a polymerization reaction between a carbon-carbon double bond group contained in the resin (a) and a carbon-carbon double bond group contained in the resin (b) is preferable from the viewpoint of continuous polymerization and high cross-linking density.

The composite resin may have structural units (hereinafter, referred to as other structural units) other than the resin (a) and the resin (b).

Other structural units can be introduced without particular limitation as long as the effect of the present invention is exhibited, but examples of thereof include an amine compound or a thiol compound in a case where it is possible to add a compound capable of bonding to the resin (a) which is an epoxy resin. In a case where the resin (a) is unsaturated polyester, it is possible to add a radical initiator or the like described below. In a case where the resin (a) is a phenolic resin, it is possible to add an epoxy compound and the like.

The proportion of the other structural units in the composite resin is preferably 0 to 30 mass % and more preferably 0 to 20 mass %.

Thermal radical initiators such as aromatic ketones, an onium salt compound, organic peroxide, a thio compound, a hexaarylbiimidazole compound, a ketoxime ester compound, an acyl phosphine oxide compound, a borate compound, an azinium compound, a metallocene compound, an active ester compound, a compound having a carbon halogen bond, an azo compound, and a bibenzyl compound are preferably used as radical initiators.

Specific examples of the thermal radical initiators include IRGACURE 184, IRGACURE 369, IRGACURE 379, IRGACURE 651, IRGACURE 907, and IRGACURE 819 (all are manufactured by BASF SE), DAROCUR 4265 and DAROCUR TPO (all are manufactured by Merck KGaA), PERHEXA H, PERHEXA HC, PERHEXA C, PERHEXA V, PERHEXA 22, PERBIJTYL H, PERCUMYL D, PERBUTYL P, PERBUTYL C, PERBUTYL D, PERHEXYL D, PERHEXA 25B, PERHEXINE 25B, PEROYL L, NYPER BW, NYPER BMT-K40. NYPER BMT-M, PERBUTYL PV. PERHEXA 25O, PEROKU O, PERHEXYL O, PERBUTYL O, PERBUTYL L, PERBUTYL 355, PERHEXYL 1, PERBUTYL, PERBUTYL E, PERHEXA 257, PERBUTYL A, PERHEXYL Z, PERBUTYL ZT, and PERBUTYL Z (all are trade names and manufactured by NOF CORPORATION).

A radical initiator may be used singly or can be used in combination of two or more thereof.

A resin material for an acoustic lens of the embodiment of the present invention may contain the resin (a) and the resin (b) in a form of a blended resin. In a case of preparing the blended resin, a reaction of bonding the resin (a) to the resin (b) is not actively caused (for example, heating), but a part of the resin (a) may be bonded to a part of the resin (b) in a blending step.

The ratio of a content mass mb of the resin (b) to a content mass ma of the resin (a) in the resin material of the embodiment of the present invention is preferably ma:mb=30:70 to 70:30, more preferably 35:65 to 65:35, and still more preferably 40:60 to 60:40. In a case where the content mass ratio is within the above-described ranges, the acoustic sensitivity of an acoustic lens is further enhanced.

Therefore, it is possible to make acoustic impedance of the acoustic lens closer to an acoustic impedance value of a living body and to further increase the tear strength of the acoustic lens.

Here, the content mass ma of the resin (a) and the content mass mb of the resin (b) in the resin material of the embodiment of the present invention can be calculated, for example, from a charged amount (mass ratio) during synthesis.

The composite resin used in the present invention may be used singly or in a combination of two or more thereof. In addition, the above-described resin (a) and resin (b) in the resin material of the embodiment of the present invention may be one kind or two or more kinds.

A gel fraction of the resin material for an acoustic lens of the embodiment of the present invention is preferably greater than or equal to 70 mass %, more preferably greater than or equal to 80 mass %, and still more preferably greater than or equal to 90 mass %. A substantial upper limit is 100 mass %. As the gel fraction is higher, the bonding between the resin (a) and the resin (b) progresses and the molecular weight becomes higher, which shows that solubility in a solvent deteriorates. In a case where the gel fraction of the resin material for an acoustic lens of the embodiment of the present invention is within the above-described ranges, the phase separation between the resin (a) and the resin (b) is suppressed and the acoustic sensitivity of the acoustic lens can be more enhanced.

The gel fraction can be measured through the method described in the section of the examples.

The acoustic impedance of the acoustic lens obtained from the resin material of the embodiment of the present invention is preferably close to an acoustic impedance value of a living body and more preferably 1.3 Mrayls, that is, greater than or equal to $1.3 \times 10^6$ kg/m$^2$/s. For this reason, the density of the acoustic lens of the embodiment of the present invention is preferably 1.05 g/cm$^3$ to 2.00 g/cm$^3$, more preferably 1.07 g/cm$^3$ to 1.80 g/cm$^3$, and still more preferably 1.10 g/cm$^3$ to 1.60 g/cm$^3$. Here, the value of the density is a value obtained by rounding off the third decimal point. The density of the acoustic lens of the embodiment of the present invention can be measured, for example, through the method described in the examples below, or can be calculated from the density of each resin. In the acoustic lens of the embodiment of the present invention, the density of a mixture or a composite resin of the resin (a) and the resin (b) is particularly preferably within the above-described ranges.

(4) Other Additives

The resin material for an acoustic lens of the embodiment of the present invention can be obtained by appropriately formulating filler, a catalyst, a solvent, a dispersant, a pigment, a dye, an antistatic agent, a flame retardant, a thermal conductivity enhancer, a vulcanization retardant, and the like with each other.

—Filler—

Since the resin material for an acoustic lens of the embodiment of the present invention does not contain inorganic filler, it is possible to produce a resin sheet having excellent characteristics. However, the resin material for an acoustic lens of the embodiment of the present invention may contain filler.

Any filler that is used in the resin material for an acoustic lens can be used as the filler without particular limitation, and specific examples thereof include inorganic compound particles.

Examples of an inorganic compound in the inorganic compound particles include silicon oxide (silica), silicon carbide, boron nitride, alumina, barium sulfate, cerium oxide, calcium carbonate, aluminum nitride, calcium oxide, vanadium oxide, silicon nitride, barium carbonate, titanium carbide, titanium nitride, copper oxide, zirconium carbide, tungsten carbide, magnesium oxide, titanium oxide, iron oxide, zinc oxide, zirconium oxide, barium oxide, tin oxide, and ytterbium oxide. Any one selected from the group consisting of silica, silicon carbide, boron nitride, alumina, barium sulfate, or cerium oxide is preferable, any one selected from the group consisting of silica, alumina, barium sulfate, or cerium oxide is more preferable, and silica is still more preferable.

In a case where the resin material for an acoustic lens contains the inorganic compound particles, it is possible to obtain an effect of improving the acoustic impedance and the mechanical strength (such as tear strength and hardness) of the acoustic lens obtained from the resin material.

The average primary particle diameter of the inorganic compound particles is preferably greater than 16 nm and less than 100 nm, more preferably 5 nm to 90 nm, still more preferably 10 nm to 80 nm, and particularly preferably 15 nm to 70 nm from the viewpoints of suppressing increase in the acoustic attenuation of the acoustic lens and improving the tear strength.

Here, the average primary particle diameter means a volume average particle diameter. The volume average particle diameter can be obtained by, for example, measuring the particle diameter distribution using a laser diffraction scattering type particle diameter distribution measurement apparatus (for example, trade name "LA910" manufactured by HORIBA, Ltd.). In the present specification, for inorganic compound particles of which the average primary particle diameter has not been disclosed in the catalog or for inorganic compound particles newly manufactured, the average primary particle diameter is obtained through the above-described measurement method.

Here, the average primary particle diameter of the inorganic compound particles means an average primary particle diameter in a state in which the surface treatment has been performed.

The inorganic compound particles may be used singly or in a combination of two or more thereof.

The specific surface area of the inorganic compound particles is preferably 1 to 400 m$^2$/g, more preferably 5 to 200 m$^2$/g, and particularly preferably 10 to 100 m$^2$/g from the viewpoint of improving the hardness and/or the mechanical strength of the acoustic lens.

The surfaces of the inorganic compound particles are preferably subjected to a treatment (modification) and more preferably subjected to surface treatment with a silane compound.

By subjecting the inorganic compound particles to surface treatment with a silane compound, an interaction with the polymer used in the present invention which has a siloxane bond becomes stronger and affinity becomes higher. Therefore, it is considered that it is possible to finely disperse inorganic compound particles with a small average primary particle diameter. For this reason, the inorganic compound fine particles more favorably exhibit functions as stoppers in a case where mechanical stress is applied, and therefore, it is considered that the hardness and the mechanical strength of the resin for an acoustic lens are improved.

A usual technique may be used as a technique of the surface treatment. Examples of the technique of the surface treatment using a silane compound include a technique of performing surface treatment using a silane coupling agent and a technique of performing coating using a silicone compound.

(i) Silane Coupling Agent

A silane coupling agent having a hydrolyzable group is preferable as a silane coupling agent from the viewpoint of improving the hardness and/or the mechanical strength of an acoustic lens. Surface modification of inorganic compound particles is performed such that a hydrolyzable group in a silane coupling agent becomes a hydroxyl group after being hydrolyzed using water and this hydroxyl group is subjected to a dehydration and condensation reaction with a hydroxyl group on the surfaces of the inorganic compound particles, thereby improving the hardness and/or the mechanical strength of obtained acoustic lens. Examples of the hydrolyzable group include an alkoxy group, an acyloxy group, and a halogen atom.

In a case where the surfaces of inorganic compound particles are hydrophobically modified, affinity between the inorganic compound particles, and the vinyl silicone and the hydrosilicone becomes favorable, and therefore, the hardness and the mechanical strength of obtained acoustic lens are improved, which is preferable.

Examples of a silane coupling agent having a hydrophobic group as a functional group include alkoxysilanes such as methyltrimethoxysilane (MTMS), dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyltriethoxysilane, and decyltrimethoxysilane; chlorosilanes such as methyltrichlorosilane, dimethyldichlorosilane, trimethylchlorosilane, and phenyltrichlorosilane; and hexamethyldisilazane (HMDS).

In addition, examples of a silane coupling agent having a vinyl group as a functional group include alkoxysilanes such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane and vinylmethyldichlorosilane: and divinyltetramethyldisilazane.

As the silane coupling agent, a trialkylsilylating agent is preferable and a trimethylsilylating agent is more preferable.

Examples of the silane compound include the above-described silane coupling agents and a silane coupling agent in which a functional group in a silane coupling agent is substituted with an alkyl group.

In addition, examples of the trimethylsilylating agent include trimethylchlorosilane and hexamethyldisilazane (HMDS) described in the above-described silane coupling agent, and methyltrimethoxysilane (MTMS) and trimethylmethoxysilane which are silane coupling agents in which a functional group is substituted with an alkyl group.

Examples of a commercially available silane coupling agent include hexamethyldisilazane (HMDS) (trade name: HEXAMETHYLDISILAZANE (SIH6110.1) manufactured by GELEST, INC.).

A hydroxyl group existing on the surfaces of inorganic compound particles is covered with a trimethylsilyl group through a reaction with hexamethyldisilazane (HMDS), methyltrimethoxysilane (MTMS), trimethylmethoxysilane, and the like and the surfaces of the inorganic compound particles are hydrophobically modified.

In the present invention, the silane coupling agent may be used singly or in a combination of two or more thereof.

(ii) Silicone Compound

A silicone compound with which the inorganic compound particles are coated may be a polymer formed through siloxane bonding.

Examples of the silicone compound include a silicone compound in which all or a part of side chains and/or terminals of polysiloxane has become a methyl group, a silicone compound in which a part of a side chain is a hydrogen atom, a modified silicone compound in which organic groups such as an amino group and/or an epoxy group is introduced into all or a part of side chains and/or terminals, and a silicone resin having a branched structure. The silicone compound may be either of a linear structure or a cyclic structure.

Examples of the silicone compound in which all or a part of side chains and/or terminals of polysiloxane has become a methyl group include monomethylpolysiloxane such as polymethylhydrosiloxane (hydride terminated), polymethylhydrosiloxane (trimethylsiloxy terminated), polymethylphenylsiloxane (hydride terminated), and polymethylphenylsiloxane (trimethylsiloxy terminated): and dimethylpolysiloxanes such as dimethylpolysiloxane (hydride terminated), dimethylpolysiloxane (trimethylsiloxy terminated), and cyclic dimethylpolysiloxane.

Examples of the silicone compound in which a part of side chains is a hydrogen atom include methylhydrosiloxane-dimethylsiloxane copolymer (trimethylsiloxy terminated), methylhydrosiloxane-dimethylsiloxane copolymer (hydride terminated), polymethylhydrosiloxane (hydride terminated), polymethylhydrosiloxane (trimethylsiloxy terminated), polyethylhydrosiloxane (triethylsiloxy terminated), polyphenyl-(dimethylhydrosiloxy) siloxane (hydride terminated), methylhydrosiloxane-phenylmethylsiloxane copolymer (hydride terminated), methylhydrosiloxane-octylmethylsiloxane copolymer, and methylhydrosiloxane-octylmethylsiloxane-dimethylsiloxane terpolymer.

In addition, examples of modified silicone into which an organic group is introduced include reactive silicone into which an amino group, an epoxy group, a methoxy group, a (meth)acryloyl group, a phenol group, a carboxylic anhydride group, a hydroxy group, a mercapto group, a carboxyl group, and/or an organic group of a hydrogen atom are introduced; and non-reactive silicone modified with polyether, aralkyl, fluoroalkyl, long chain alkyl, long chain aralkyl, higher fatty acid ester, higher fatty acid amide, and/or polyether methoxy. Inorganic compound particles coated with a silicone compound can be obtained through a usual method. For example, the inorganic compound particles can be obtained by being mixed and stirred in dimethylpolysiloxane for a certain period of time and being filtered.

In addition, in a case of using reactive modified silicone as a silicone compound, surface modification of inorganic compound particles is performed through a reaction of an organic group with a hydroxyl group on the surfaces of the inorganic compound particles, and therefore, the hardness and/or the mechanical strength of an obtained acoustic lens is improved.

An Example of the commercially available silicone compound includes methyl hydrogen silicone oil (MHS) (trade name: KF-99, manufactured by Shin-Etsu Chemical Co., Ltd.) which is polymethylhydrosiloxane (trimethylsiloxy terminated).

The degree of surface modification of the inorganic compound particles, that is, the hydrophobicity of the inorganic compound particles can be examined by the following methanol hydrophobicity.

The methanol hydrophobicity of the inorganic compound particles which is calculated through the following methanol titration test is preferably 40 to 80 mass %, more preferably 50 to 80 mass %, and still more preferably 60 to 80 mass %. Here, the larger the methanol hydrophobicity, the higher the hydrophobicity, and the smaller the methanol hydrophobicity, the higher the hydrophilicity.

50 ml of ion exchange water and 0.2 g of inorganic compound particles as samples are placed in a beaker at 25° C. and stirred with a magnetic stirrer, methanol is added dropwise thereto from a burette, and the amount (Xg) of methanol added dropwise until the whole sample settles is measured. The methanol hydrophobicity is calculated using the following equation.

Methanol hydrophobicity (mass %)=$\{X/(50+X)\}\times 100$

In a case where the methanol hydrophobicity is within the above-described preferred ranges, it is possible to suppress increase in viscosity of the resin material for an acoustic lens and decrease in acoustic sensitivity of the acoustic lens.

The Wardell's sphericity of a primary particle of the inorganic compound particles is preferably 0.7 to 1, more preferably 0.8 to 1, and still more preferably 0.9 to 1.

Here, the "Wardell's sphericity" (refer to Chemical Engineering Handbook published by Maruzen Inc.) is an index obtained by measuring the sphericity of a particle as (diameter of circle equal to projection area of particle)/(diameter of minimum circle circumscribing projection image of particle). A particle having the index closer to 1.0 means a particle closer to a true sphere.

It is possible to use, for example, a scanning electron microscope (SEM) photograph can be used to measure the Wardell's sphericity (hereinafter, also simply referred to as sphericity). Specifically, for example, about 100 primary particles are observed using the SEM photograph, and each sphericity thereof is calculated. An average value obtained by dividing the total of the calculated sphericities by the number of observed primary particles is regarded as the sphericity.

In a case where the Wardell's sphericity is within the above-described preferred ranges, it is considered that the acoustic sensitivity is improved because the area of the acoustic wave hitting the inorganic compound particles becomes smaller in a case where the acoustic lens is irradiated with the acoustic wave. In particular, the shapes of the inorganic compound particles are preferably spherical and more preferably truly spherical in that the acoustic sensitivity is more effectively improved within the ranges of the specific average primary particle diameter of the inorganic compound particles.

In this specification, the "true spherical shape" also includes a slightly distorted sphere of which the Wardell's sphericity is within a range of 0.9 to 1.

Of the inorganic compound particles, the silica particles are roughly classified into combustion method silica (that is, fumed silica) obtained by burning a silane compound, deflagration method silica obtained by explosively burning metallic silicon powder, wet-type silica (among which silica synthesized under alkaline conditions is referred to as precipitation method silica and silica synthesized under acidic conditions is referred to as gel method silica) obtained through a neutralization reaction with sodium silicate and mineral acid, and sol-gel method silica (so-called Stoeber method) obtained through hydrolysis of hydrocarbyloxysilane depending on its production method.

Preferred examples of a method for producing truly spherical silica particles include an explosion method and a sol-gel method.

The sol-gel method is a method of obtaining hydrophilic spherical silica particles essentially consisting of $SiO_2$ units by hydrolyzing and condensing a hydrocarbyloxysilane (preferably tetrahydrocarbyloxysilane) or a partial hydrolytic condensation product thereof or a combination thereof.

In addition, the hydrophobic treatment of the surfaces of the silica particles can also be carried out by introducing $R^3_3SiO_{1/2}$ units ($R^3$'s are the same as or different from each other and are substituted or unsubstituted monovalent hydrocarbon groups having 1 to 20 carbon atoms) onto the surfaces of hydrophilic spherical silica particles.

Specifically, the hydrophobic treatment thereof can be carried out, for example, through methods disclosed in JP2007-099582A and JP2014-114175A.

—Catalyst—

Examples of the catalyst include platinum or a platinum-containing compound (hereinafter, also simply referred to as a platinum compound). Any platinum or platinum compound can be used.

Specific examples thereof include a catalyst in which platinum black or platinum is carried on an inorganic compound, carbon black, or the like; platinum chloride or an alcohol solution of platinum chloride; a complex salt of platinum chloride and olefin; and a complex salt of platinum chloride and vinyl siloxane. The catalyst may be used singly, or in a combination of two or more thereof.

The catalyst is necessary in the hydrosilylation reaction in which the Si—H group of the hydrosilicone is added to the vinyl group of the vinyl silicone. As the hydrosilylation reaction (addition vulcanization reaction) proceeds, vinyl silicone is cross-linked with hydrosilicone to form silicone resin.

Here, the catalyst may be contained in the resin material for an acoustic lens of the embodiment of the present invention. Alternately, the catalyst may not be contained in the resin material for an acoustic lens, but brought into contact with the resin material for an acoustic lens in a case of molding or the like using the resin material for an acoustic lens.

The latter case is preferable.

Examples of commercially available platinum catalyst include platinum compounds (trade name of PLATINUM CYCLOVINYLMETHYLSILOXANE COMPLEX IN CYCLIC METHYLVINYLSILOXANES (SIP6832.2) with 2 mass % of Pt concentration; and a trade name of PLATINUM DIVINYLTETRAMETHYLDISILOXANE COMPLEX IN VINYL-TERMINATED POLYDIMETHYLSILOXANE (SIP6830.3) with 3 mass % of Pt concentration, all of which are manufactured by GELEST, INC.).

In a case where a catalyst is contained in the resin material for an acoustic lens of the embodiment of the present invention, the content of the catalyst present with respect to 100 parts by mass of a polysiloxane mixture is not particularly limited, but is preferably 0.00001 to 0.05 parts by mass, more preferably 0.00001 to 0.01 parts by mass, still more preferably 0.00002 to 0.01 parts by mass, and particularly preferably 0.00005 to 0.005 parts by mass from the viewpoint of reactivity.

In addition, it is possible to control the vulcanization temperature by selecting an appropriate platinum catalyst. For example, platinum-vinyldisiloxane is used for room temperature vulcanization (RTV) at lower than or equal to 50° C. and platinum-cyclic vinylsiloxane is used for high temperature vulcanization (HTV) at higher than or equal to 130° C.

—Vulcanization Retardant—

In the present invention, a vulcanization retardant for vulcanization reaction can be appropriately used. The vulcanization retardant is used for delaying the above-described addition vulcanization reaction and examples thereof include a low molecular weight vinylmethylsiloxane homopolymer (trade name: VMS-005 manufactured by GELEST, INC.).

The vulcanization rate, that is, the working time can be adjusted depending on the content of the vulcanization retardant.

<Method for Producing Resin Material for Acoustic Lens and Resin Sheet for Acoustic Lens>

The resin material for an acoustic lens of the embodiment of the present invention can be prepared through a usual method.

For example, the resin material for an acoustic lens can be obtained by kneading resins (a) and (b) and the above-described other components which may be contained at 70° C. to 300° C. for 0.5 to 10 hours using a Laboplast mill, a kneader, a pressure kneader, a Banbury mixer (continuous kneader), or a kneading device with two rolls. The order of mixing the components is not particularly limited.

It is possible to obtain a resin sheet for an acoustic lens, for example, by thermally pressing the resin material for an acoustic lens of the embodiment of the present invention which has been obtained in this manner. The thermal press method is not particularly limited, and can be performed through a usual method. An example thereof includes an aspect in which thermal pressing is performed at 70° C. to 300° C. for 1 to 10 minutes at a pressure of 5 to 30 MPa using an apparatus such as MINI TEST PRESS MP-WNL (trade name manufactured by Toyo Seiki Seisaku-sho, Ltd.).

It is possible to obtain a resin material for an acoustic lens and a resin sheet for an acoustic lens obtained by bonding resins (a) to each other through a reaction between functional groups contained in the resins (a) through heating in the above-described kneading step and/or a thermal press step. In particular, in a case where the resins (a) are thermosetting resins, it is possible to obtain a resin material for an acoustic lens and a resin sheet for an acoustic lens which contain the resins (a) that have been heated and vulcanized through the above-described kneading step and/or a thermal press step.

In addition, in a case where the resin (b) has functional groups capable of bonding to each other through a reaction between an epoxy group contained in the resin (a), a carbon-carbon double bond group, a methylol group, and/or a phenolic hydroxyl group, it is possible to obtain a resin material for an acoustic lens and a resin sheet for an acoustic lens in which a bonding through a reaction between functional groups is formed in addition to heating and vulcanizing through the above-described kneading step and/or a thermal press step and which contains a composite resin obtained by bonding of at least a part of the resin (a) to a part of at least the resin (b).

<Tear Strength and Acoustic Characteristics of Resin Sheet for Acoustic Lens>

The resin sheet for an acoustic lens is obtained by molding the resin material for an acoustic lens of the embodiment of the present invention through thermal pressing or the like.

Hereinafter, the tear strength and the acoustic characteristics of a resin sheet for an acoustic lens will be described in detail.

Here, ultrasonic characteristics among the acoustic characteristics will be described. However, the acoustic characteristics are not limited to the ultrasonic characteristics, and relates to acoustic characteristics at an appropriate frequency which is selected in accordance with a test object, measurement conditions, and the like.

[Tear Strength]

The tear strength is preferably greater than or equal to 1 N/cm, more preferably greater than or equal to 5 N/cm, and still more preferably greater than or equal to 10 N/cm. The tear strength can be measured through the method described in the section of the examples.

[Acoustic Impedance]

The acoustic impedance is preferably close to that of a living body, more preferably 1.10 to $1.75 \times 10^6$ kg/m²/sec, more preferably 1.20 to $1.70 \times 10^6$ kg/m²/sec, still more preferably 1.25 to $1.65 \times 10^6$ kg/m²/sec, and particularly preferably 1.30 to $1.60 \times 10^6$ kg/m²/sec.

The acoustic impedance of a silicone resin can be obtained through the measurement method described in the section of examples.

[Acoustic (Ultrasonic) Attenuation and Sensitivity]

The acoustic (ultrasonic) attenuation and sensitivity can be measured through the method described in the section of the examples.

In an evaluation system in the present invention, the acoustic (ultrasonic) sensitivity is preferably greater than or equal to −70 dB and more preferably greater than or equal to −68 dB.

The acoustic lens of the embodiment of the present invention containing the resin material for an acoustic lens of the embodiment of the present invention can be used, for example, in an acoustic wave probe. In addition, the acoustic wave probe can be preferably used in an acoustic wave measurement apparatus. The acoustic wave measurement apparatus of the embodiment of the present invention is not limited to an ultrasound diagnostic apparatus or a photoacoustic wave measurement apparatus, and is referred to as an apparatus that receives an acoustic wave which has been reflected or generated from an object and displays the received acoustic wave as an image or a signal strength.

Particularly, the resin material for an acoustic lens of the embodiment of the present invention can suitably be used in: a material of an acoustic lens of an ultrasound diagnostic apparatus and an acoustic lens in a photoacoustic wave measurement apparatus or an ultrasound endoscope; and a material or the like of an acoustic lens in an ultrasound probe including capacitive micromachined ultrasonic transducers (cMUT) as an ultrasonic transducer array.

Specifically, the resin material for an acoustic lens of the embodiment of the present invention is preferably applied to, for example, an acoustic lens of an ultrasound diagnostic apparatus disclosed in JP2005-253751A and JP2003-169802A or an acoustic wave measurement apparatus such as a photoacoustic wave measurement apparatus disclosed in JP2013-202050A, JP2013-188465A, JP2013-180330A, JP2013-158435A, JP2013-154139A, or the like.

<<Acoustic Wave Probe>>

A configuration of an acoustic wave probe of the embodiment of the present invention will be described below in more detail based on a configuration of an ultrasound probe in an ultrasound diagnostic apparatus which is described in FIG. 1. The ultrasound probe is a probe which particularly uses an ultrasonic wave as an acoustic wave in an acoustic wave probe. For this reason, a basic configuration of the ultrasound probe can be applied to the acoustic wave probe as it is.

—Ultrasound Probe—

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end (the surface coming into contact with a living body which is a test object) as shown in FIG. 1. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

Inorganic piezoelectric bodies of so-called ceramics obtained by polarizing crystals, single crystals such as $LiNbO_3$, $LiTaO_3$, and $KNbO_3$, thin films of ZnO and AlN, $Pb(Zr,Ti)O_3$-based sintered body, and the like are widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent broadband characteristics, and excellent mass productivity and has less characteristic variations, is obtained is disclosed in JP2011-071842A or the like.

In the present invention, it is possible to preferably use any piezoelectric element material.

<Backing Material>

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

<Acoustic Matching Layer>

The acoustic matching layer 2 is provided in order to reduce the difference in acoustic impedance between the piezoelectric element layer 3 and a test object and to efficiently transmit and receive an ultrasonic wave.

<Acoustic Lens>

The acoustic lens 1 is provided in order to improve resolution by making an ultrasonic wave converge in a slice direction using refraction. In addition, it is necessary for the acoustic lens to achieve matching of an ultrasonic wave with acoustic impedance (1.4 to $1.7 \times 10^6$ $kg/m^2/sec$ in a case of a human body) of a living body which is a test object after being closely attached to the living body and to reduce ultrasonic attenuation of the acoustic lens 1 itself.

That is, sensitivity of transmission and reception of an ultrasonic wave is improved using a material of which the acoustic velocity is sufficiently lower than that of a human body, the ultrasound attenuation is low, and the acoustic impedance is close to a value of the skin of a human body, as the material of the acoustic lens 1.

The resin material for an acoustic lens of the embodiment of the present invention can be preferably used in an acoustic lens of which the acoustic impedance is $1.7 \times 10^6$ $kg/m^2/sec$. The lower limit is preferably greater than or equal to $1.2 \times 10^6$ $kg/m^2/sec$.

The aspect described in the section of the above-described resin sheet for an acoustic lens can be preferably applied for the details of the acoustic impedance of the acoustic lens.

The operation of the ultrasound probe 10 having such a configuration will be described. The piezoelectric element layer 3 is resonated after applying voltage to the electrodes provided on both sides of a piezoelectric element, and an ultrasound signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

Particularly, a remarkable effect of improving the sensitivity can be checked from a transmission frequency of an ultrasonic wave of greater than or equal to about 5 MHz using the acoustic lens obtained from the resin material for an acoustic lens of the embodiment of the present invention as a general medical ultrasonic transducer. Particularly, a remarkable effect of improving the sensitivity can particularly be expected from a transmission frequency of an ultrasonic wave of greater than or equal to 10 MHz.

Hereinafter, an apparatus in which the acoustic lens obtained from the resin material for an acoustic lens of the embodiment of the present invention exhibits a function particularly regarding conventional problems will be described in detail.

The resin material for an acoustic lens of the embodiment of the present invention exhibits an excellent effect even with respect to other apparatuses disclosed below.

—Ultrasound Probe Including Capacitive Micromachined Ultrasonic Transducer (cMUT)—

In a case where cMUT devices disclosed in JP2006-157320A, JP2011-071842A. and the like are used in an ultrasonic diagnostic transducer array, the sensitivity thereof generally becomes low compared to a transducer in which usual piezoelectric ceramics (PZT) is used.

However, it is possible to make up for deficient sensitivity of cMUT using the acoustic lens obtained from the resin material for an acoustic lens of the embodiment of the present invention. Accordingly, it is possible to approximate the sensitivity of cMUT to performance of a conventional transducer.

The cMUT device is manufactured through MEMS technology. Therefore, it is possible to provide an inexpensive ultrasound probe, of which mass productivity is higher than that of a piezoelectric ceramics probe, to the market.

—Photoacoustic Wave Measurement Apparatus Using Photo-Ultrasound Imaging—

Photoacoustic imaging (photo acoustic imaging: PAI) disclosed in JP2013-158435A or the like displays a signal strength of an ultrasonic wave or an image obtained by imaging the ultrasonic wave generated in a case where human tissue is adiabatically expanded using light (magnetic wave) with which the interior of a human body is irradiated.

Here, the amount of an acoustic pressure of an ultrasonic wave generated through light irradiation is minute, and therefore, there is a problem in that it is difficult to observe deeper regions of a human body.

However, it is possible to exhibit an effect effective for the problem using the acoustic lens obtained from the resin material for an acoustic lens of the embodiment of the present invention.

—Ultrasound Endoscope—

In an ultrasonic wave in an ultrasound endoscope disclosed in JP2008-311700A or the like, a signal line cable is structurally long compared to that of a transducer for a body surface, and therefore, there is a problem of improving the sensitivity of the transducer accompanied by loss of the cable. Regarding this problem, it is said that there are no effective means for improving the sensitivity due to the following reasons.

First, in a case of an ultrasound diagnostic apparatus for a body surface, it is possible to install an amplifier circuit, an AD conversion IC, or the like at a distal end of the transducer. In contrast, the ultrasound endoscope is inserted into a body. Therefore, there is a small installation space within the transducer, and thus, it is difficult to install the amplifier circuit, the AD conversion IC, or the like at a distal end of the transducer.

Secondly, it is difficult to apply a piezoelectric single crystal employed in the transducer in the ultrasound diagnostic apparatus for a body surface onto a transducer with an ultrasonic transmission frequency of greater than or equal to 7 to 8 MHz due to physical properties and processing suitability. However, an ultrasonic wave for an endoscope is generally a probe having an ultrasonic transmission frequency of greater than or equal to 7 to 8 MHz, and therefore, it is also difficult to improve the sensitivity using piezoelectric single crystal material.

However, it is possible to improve the sensitivity of the endoscope ultrasonic transducer using the acoustic lens obtained from the resin material for an acoustic lens of the embodiment of the present invention.

In addition, even in a case of using the same ultrasonic transmission frequency (for example, 10 MHz), the efficacy is particularly exhibited in a case of using the acoustic lens obtained from the resin material for an acoustic lens of the embodiment of the present invention in the ultrasonic transducer for an endoscope.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like. Hereinafter, the room temperature means 25° C.

Examples

<Production of Resin Sheet>

(1) Production of Resin Sheet Nos. 101 to 112 and c13 to c17

80 parts by mass of an epoxy resin 4004P (trade name manufactured by Mitsubishi Chemical Corporation) as a resin (a) and 20 parts by mass of KF-96-50cs (trade name manufactured by Shin-Etsu Chemical Co., Ltd.) as a resin (b) were kneaded for 2 hours at 150° C. with a Laboplast mill (manufactured by Toyo Seiki Seisaku-sho, Ltd.). Thereafter, the kneaded resin material was subjected to thermal press treatment to produce a resin sheet No. 101 having a length of 60 mm, a width of 60 mm, and a thickness of 2 mm.

Here, in the thermal press treatment, the resin material was filled into a mold and a film is formed by performing pressing at 10 MPa for 5 minutes while setting the pressing temperature at 200° C. using "MINI TEST PRESS MP-WNL" manufactured by Toyo Seiki Seisaku-sho, Ltd.

Resin sheets Nos. 102 to 112 and c13 to c17 were produced in the same manner as in the production of the resin sheet No. 101 except that the type and the formulation ratio of the resin (a) and the resin (b) described in Table 1.

(2) Production of Resin Sheet No. c11

96 parts by mass of vinyl terminated polydimethylsiloxane DMS-V41 (trade name manufactured by Gelest, Inc.), 4 parts by mass of a methylhydrosiloxane-dimethylsiloxane copolymer HMS-301 (trade name manufactured by Gelest, Inc.), and 0.03 parts by mass of a platinum catalyst SIP 6830.3 (trade name manufactured by Gelest, Inc.) were mixed with each other to obtain a resin material which was then thermally vulcanized at 150° C. and 10 MPa for 5 minutes using the above-described apparatus for performing thermal press treatment on the resin material to produce a resin sheet No. c11 with a length of 60 mm, a width of 60 mm, and a thickness of 2 mm.

(3) Production of Resin Sheet No. c12 77 parts by mass of vinyl terminated polydimethylsiloxane DMS-V41 (a trade name manufactured by Gelest), 3 parts by mass of a methylhydrosiloxane-dimethylsiloxane copolymer HMS-301 (a trade name manufactured by Gelest), 20 parts by mass of fumed silica AEROSIL R974 (a trade name manufactured by NIPPON AEROSIL CO., LTD., an average primary particle diameter of 12 nm, dimethyldichlorosilane surface treatment), and 0.05 parts by mass of a platinum catalyst SIP 6830.3 (manufactured by Gelest) were mixed with each other to obtain a resin material which was then thermally vulcanized at 150° C. and 10 MPa for 5 minutes using the above-described apparatus for performing thermal press treatment on the resin material to produce a resin sheet No. c12 with a length of 60 mm, a width of 60 mm, and a thickness of 2 mm.

<Evaluation of Physical Properties, Ultrasonic Characteristics, and Mechanical Characteristics>

The resin sheets No. 101 to 112 and c11 to c17 produced above were evaluated as follows.

1. Gel Fraction 100 mg of a sample obtained by cutting each resin sheet produced above was immersed in 10 g of tetrahydrofuran at room temperature for 24 hours, and was then taken out and dried at 100° C. for 2 hours. A gel fraction was measured using the following formula from a sample mass $m_0$ before the immersion and a sample mass $m_{24}$ after the immersion and dry.

Gel fraction (mass %)=$(m_{24}/m_0) \times 100$

2. Density

The density of each of the obtained resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999).

Here, in a case where components other than the resin (a) and the resin (b) are not contained in the resin sheet, the density measured through the above-described method corresponds to the density of the resin (a) and the resin (b).

3. Acoustic (Ultrasonic) Sensitivity

A sinusoidal signal (a wave) of 10 MHz which had been output from an ultrasound oscillator (a function generator with a trade name of "FG-350" manufactured by IWATSU ELECTRIC CO., LTD.) was input into an ultrasound probe (manufactured by JAPAN PROBE), and an ultrasound pulse wave with a center frequency of 10 MHz was generated in water from the ultrasound probe. The magnitude of the amplitude before and after the generated ultrasonic wave passed through each of the obtained resin sheet with a thickness of 2 mm was measured in a water temperature environment of 25° C. using an ultrasound receiver (an oscilloscope with a trade name of "VP-5204A" manufactured by Matsushita Electric Industrial Co., Ltd.). The acoustic (ultrasonic) attenuation of each material was compared with each other by comparing the acoustic (ultrasonic) sensitivities of each material.

The acoustic (ultrasonic) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained when the ultrasound oscillator receives an acoustic wave (ultrasonic wave) that the acoustic wave (ultrasonic wave) generated passes through a sheet and is reflected from an opposite side of the sheet. The higher the acoustic (ultrasonic) sensitivity is, the smaller the acoustic (ultrasonic) attenuation is.

Acoustic (Ultrasonic) sensitivity=$20 \times \mathrm{Log}(Vs/Vin)$

The acoustic wave (ultrasonic) sensitivity was evaluated according to the following evaluation criteria. In this test, the evaluation of higher than or equal to "C" is an acceptance level.

(Evaluation Criteria)
AA: Greater than or equal to −66 dB
A: Greater than or equal to −68 dB and less than −66 dB
B: Greater than or equal to −70 dB and less than −68 dB
C: Greater than or equal to −72 dB and less than −70 dB
D: Less than −72 dB 4. Acoustic Impedance The density of each of the obtained resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999). The acoustic velocity of an ultrasonic wave was measured at 25° C. using a sing-around type acoustic velocity measurement apparatus (a trade name of "UVM-2 type" manufactured by Ultrasonic Engineering Co., Ltd.) in compliance with JIS Z2353 (2003) and acoustic impedance was obtained from a sum of the density and the acoustic velocity which had been measured. The acoustic impedance was evaluated according to the following evaluation criteria. In this test, the evaluation of higher than or equal to "C" is an acceptance level.

(Evaluation Criteria)
AA: Greater than or equal to $1.30 \times 10^6$ kg/m$^2$/s and less than $1.60 \times 10^6$ kg/m$^2$/s
A: Greater than or equal to $1.25 \times 10^6$ kg/m$^2$/s and less than $1.30 \times 10^6$ kg/m$^2$/s or greater than or equal to $1.60 \times 10^6$ kg/m$^2$/s and less than $1.65 \times 10^6$ kg/m is
B: Greater than or equal to $1.20 \times 10^6$ kg/m$^2$/s and less than $1.25 \times 10^6$, m$^2$/s or greater than or equal to $1.65 \times 10^6$ kg/m$^2$/s and less than $1.70 \times 10^6$ kg/m$^2$/s
C: Greater than or equal to $1.10 \times 10^6$ kg/m$^2$/s and less than $1.20 \times 10^6$ kg/m$^2$/s or greater than or equal to $1.70 \times 10^6$ kg/m$^2$/s and less than $1.75 \times 10^6$ kg/m$^2$/s
D: Less than $1.10 \times 10^6$ kg/m$^2$/s and greater than or equal to $1.75 \times 10^6$ kg/m$^2$/s 5. Tear Strength A trouser-type test piece of a resin sheet with a thickness of 2 mm was manufactured, and the tear strength was measured in compliance with JIS K6252 (2007) and evaluated according to the following evaluation criteria. In this test, the evaluation of higher than or equal to "C" is an acceptance level.

<Evaluation Criteria>
AA: Greater than or equal to 15 N/cm
A: Greater than or equal to 10 N/cm and less than 15 N/cm
B: Greater than or equal to 5 N/cm and less than 10 N/cm
C: Greater than or equal to 1 N/cm and less than 5 N/cm
D: Less than 1 N/cm The structure, physical properties, and evaluation results of the resin sheet are collectively shown in Table 1.

TABLE 1

| | Resin (a) | | Resin (b) | | |
|---|---|---|---|---|---|
| No. | Kind | Formulation ratio | Kind | Formulation ratio | Gel fraction [mass %] |
| 101 | 4004P | 80 | KF-96-50cs | 20 | 80 |
| 102 | 4004P | 80 | KF-8012 | 20 | 96 |
| 103 | 4004P | 60 | KF-8012 | 40 | 94 |
| 104 | 4004P | 40 | KF-8012 | 60 | 92 |
| 105 | EPICLON HM-101 | 40 | KF-8012 | 60 | 93 |
| 106 | FLEAMIN M | 40 | KF-6003 | 60 | 93 |
| 107 | FLEAM1N Z | 40 | KF-6003 | 60 | 95 |
| 108 | U-PICA 4015 | 40 | KF-2012 | 60 | 92 |
| 109 | U-PICA 4015 | 40 | DMS-V41 | 60 | 93 |
| 110 | U-PICA 4015 | 40 | HMS-301 | 60 | 93 |
| 111 | ARONIX M-400 | 40 | DMS-V41 | 60 | 93 |
| 112 | TD-2131 | 40 | X-22-163A | 60 | 92 |
| c11 | — | 0 | DMS-V41/HMS-301 | 96/4 | 99 |
| c12 | — | 0 | (DMS-V41/HMS-301)/silica | 77/3/20 | 99 |
| c13 | 4004P | 100 | — | 0 | 99 |
| c14 | EPICLON HM-101 | 100 | — | 0 | 99 |
| c15 | FLEAMIN M | 100 | — | 0 | 99 |
| c16 | FLEAMIN Z | 100 | — | 0 | 99 |

TABLE 1-continued

| | | | | | |
|---|---|---|---|---|---|
| c17 | U-PICA-4015 | 100 | — | | 0 | 99 |

| No. | Density [g/cm³] | Evaluation | | Tear strength | Remark |
|---|---|---|---|---|---|
| | | Acoustic attenuation | Acoustic impedance | | |
| 101 | 1.14 | B | B | AA | Present invention |
| 102 | 1.14 | A | B | AA | Present invention |
| 103 | 1.09 | A | A | AA | Present invention |
| 104 | 1.05 | A | AA | AA | Present invention |
| 105 | 1.13 | A | AA | AA | Present invention |
| 106 | 1.15 | A | AA | AA | Present invention |
| 107 | 1.15 | A | AA | AA | Present invention |
| 108 | 1.13 | AA | AA | AA | Present invention |
| 109 | 1.13 | AA | AA | AA | Present invention |
| 110 | 1.13 | AA | AA | AA | Present invention |
| 111 | 1.13 | A | AA | AA | Present invention |
| 112 | 1.13 | A | AA | AA | Present invention |
| c11 | 0.98 | A | D | D | Comparative Example |
| c12 | 1.08 | D | C | B | Comparative Example |
| c13 | 1.19 | C | D | AA | Comparative Example |
| c14 | 1.40 | C | D | AA | Comparative Example |
| c15 | 1.44 | C | D | AA | Comparative Example |
| c16 | 1.45 | C | D | AA | Comparative Example |
| c17 | 1.80 | B | D | AA | Comparative Example |

<Notes of Table 1>
(Resin (a))
4004P: Trade name, epoxy resin, manufactured by Mitsubishi Chemical Corporation
EPICLON HM-101: trade name, epoxy resin, manufactured by DIC CORPORATION
FLEAMIN M: trade name, urea resin, manufactured by Daiwa
FLEAMIN Z: trade name, melamine resin, manufactured by Daiwa
U-PICA 4015: trade name, unsaturated polyester, manufactured by U-PICA Company, Ltd.
ARONIX M-400: trade name, acrylate compound, manufactured by TOAGOSEI CO., LTD.
TD-2131: trade name, phenolic resin, manufactured by DIC CORPORATION
(Resin (b))
KF-96-50cs: trade name, silicone, manufactured by Shin-Etsu Chemical Co., Ltd.
KF-8012: trade name, amino group-containing silicone, manufactured by Shin-Etsu Chemical Co., Ltd.
KF-6003: trade name, hydroxy group-containing silicone, manufactured by Shin-Etsu Chemical Co., Ltd.
KF-2012: trade name, methacrylic group-containing silicone, manufactured by Shin-Etsu Chemical Co., Ltd.
DMS-V41: trade name, vinyl terminated polydimethylsiloxane manufactured by GELEST, INC.
HMS-301: trade name, methylhydrosiloxane-dimethylsiloxane copolymer, manufactured by GELEST, INC.
X-22-163A: trade name, epoxy group-containing silicone, manufactured by Shin-Etsu Chemical Co., Ltd.
(Silica)
Trade name "AEROSIL R974", manufactured by NIPPON AEROSIL CO., LTD., average primary particle diameter of 12 nm, surface treatment with dimethyldichlorosilane
The formulation ratio is represented by a mass ratio.

"-" indicates that the resin sheet does not contain the corresponding component.

It can be seen from Table 1 that the resin sheet in which a resin material for an acoustic lens of the embodiment of the present invention is used has an acoustic impedance close to an acoustic impedance value of a living body, has a decreasing acoustic attenuation even at a high frequency, and has an excellent tear strength.

The present invention has been described using an embodiment thereof. However, it is considered that, unless otherwise specified, even the detailed description of the invention is not limited and is necessarily widely interpreted without departing from the gist and the range of the invention shown in the attached Claims.

EXPLANATION OF REFERENCES

1: acoustic lens
2: acoustic matching layer
3: piezoelectric element layer
4: backing material
7: housing
9: cord
10: ultrasound probe

What is claimed is:
1. The resin material for an acoustic lens which is used for an acoustic wave probe lens of which an acoustic impedance is from 1.10 to $1.75 \times 10^6$ kg/m²/sec, the resin material for an acoustic lens comprising:
  a resin (a) containing at least one of an epoxy group, a carbon-carbon double bond group, a methvlol group, or a phenolic hydroxyl group; and
  a resin (b) containing a structural unit having a polvsiloxane bond, wherein the resin (a) is at least one of an epoxy resin, a phenolic resin, a urea resin, a melamine resin, or an unsaturated polyester.

2. The resin material for an acoustic lens according to claim 1, wherein the acoustic impedance is from 1.20 to $1.70 \times 10^6$ kg/m$^2$/sec.

3. The resin material for an acoustic lens according to claim 1, wherein the acoustic impedance is from 1.25 to $1.65 \times 10^6$ kg/m$^2$/sec.

4. The resin material for an acoustic lens according to claim 1, wherein the acoustic impedance is from 1.30 to $1.60 \times 10^6$ kg/m$^2$/sec.

5. An acoustic lens comprising:
a resin material for an acoustic lens, the resin material for an acoustic lens comprising:
a resin (a) containing at least one of an epoxy group, a carbon-carbon double bond group, a methylol group, or a phenolic hydroxyl group; and
a resin (b) containing a structural unit having a polysiloxane bond, wherein the resin (a) is at least one of an epoxy resin, a phenolic resin, a urea resin, a melamine resin, or an unsaturated polyester.

6. The acoustic lens according to claim 5,
wherein at least a part of the resin (a) is bonded to at least a part of the resin (b).

7. The acoustic lens according to claim 6,
wherein a bonding portion between the resin (a) and the resin (b) has an epoxy ring-opened structure formed by a reaction between an epoxy group contained in the resin (a) and at least one of an amino group and a carboxy group contained in the resin (b).

8. The acoustic lens according to claim 6,
wherein the bonding portion between the resin (a) and the resin (b) has a carbon-carbon bond formed by polymerization between the carbon-carbon double bond group contained in the resin (a) and a carbon-carbon double bond group contained in the resin (b).

9. The acoustic lens according to claim 6,
wherein the bonding portion between the resin (a) and the resin (b) has at least one of an ether bond and an imino bond formed by a reaction between the methylol group contained in the resin (a) and at least one of a hydroxy group and the amino group contained in the resin (b).

10. The acoustic lens according to claim 6,
wherein the bonding portion between the resin (a) and the resin (b) has an epoxy ring-opened structure formed by a reaction between the phenolic hydroxyl group contained in the resin (a) and an epoxy group contained in the resin (b).

11. The acoustic lens according to claim 6,
wherein the bonding portion between the resin (a) and the resin (b) has a carbon-carbon-Si bond formed by a reaction between the carbon-carbon double bond group contained in the resin (a) and a Si—H group contained in the resin (b).

12. The acoustic lens according claim 5, comprising:
a blended resin of the resin (a) and the resin (b).

13. The acoustic lens according to claim 5,
wherein a ratio of a content mass mb of the resin (b) to a ratio of a content mass ma of the resin (a) is ma:mb=30:70 to 70:30.

14. The acoustic lens according to claim 5,
wherein a density is greater than or equal to 1.05 g/cm$^3$.

15. A acoustic wave probe comprising:
the acoustic lens according to claim 5.

16. An acoustic wave measurement apparatus comprising:
the acoustic wave probe according to claim 15.

17. An ultrasound diagnostic apparatus comprising:
the acoustic wave probe according to claim 15.

18. A photoacoustic wave measurement apparatus comprising:
the acoustic lens according to claim 5.

19. An ultrasound endoscope comprising:
the acoustic lens according to claim 5.

* * * * *